(12) United States Patent
Labitzke (10) Patent No.: US 9,456,857 B2
(45) Date of Patent: Oct. 4, 2016

(54) APPARATUS FOR STABILIZING LONG BONE FRACTURES

(75) Inventor: Reiner Labitzke, Schwerte (DE)

(73) Assignee: H&R SPECIAL SPRINGS L.P., Bellingham, WA (US)

(*) Notice: Subject to any disclaimer, the term of this patent is extended or adjusted under 35 U.S.C. 154(b) by 1068 days.

(21) Appl. No.: 12/417,213

(22) Filed: Apr. 2, 2009

(65) Prior Publication Data

US 2009/0254087 A1 Oct. 8, 2009

(30) Foreign Application Priority Data

Apr. 7, 2008 (DE) .................. 10 2008 017 741

(51) Int. Cl.
| | |
|---|---|
| A61B 17/72 | (2006.01) |
| A61B 17/68 | (2006.01) |
| A61B 17/88 | (2006.01) |
| A61B 17/86 | (2006.01) |
| A61B 17/92 | (2006.01) |

(52) U.S. Cl.
CPC ......... *A61B 17/7208* (2013.01); *A61B 17/685* (2013.01); *A61B 17/7283* (2013.01); *A61B 17/8872* (2013.01); *A61B 17/7266* (2013.01); *A61B 17/869* (2013.01); *A61B 17/921* (2013.01)

(58) Field of Classification Search
CPC ........................ A61B 17/72–17/7291
USPC ....................................... 606/62–68
See application file for complete search history.

(56) References Cited

U.S. PATENT DOCUMENTS

| | | | | |
|---|---|---|---|---|
| 4,628,923 | A * | 12/1986 | Medoff | 606/65 |
| 4,959,064 | A * | 9/1990 | Engelhardt | 606/65 |
| 5,779,705 | A * | 7/1998 | Matthews | 606/67 |
| 6,174,312 | B1 * | 1/2001 | Laminger | 606/63 |
| 6,461,360 | B1 * | 10/2002 | Adam | 606/67 |
| 2002/0055737 | A1 * | 5/2002 | Lieberman | 606/61 |
| 2002/0139208 | A1 * | 10/2002 | Yatskov | 74/424.77 |
| 2005/0056979 | A1 * | 3/2005 | Studer et al. | 267/118 |
| 2006/0129247 | A1 * | 6/2006 | Brown et al. | 623/23.46 |
| 2007/0032123 | A1 * | 2/2007 | Timm et al. | 439/395 |
| 2007/0233172 | A1 * | 10/2007 | Gellman | 606/194 |

FOREIGN PATENT DOCUMENTS

| | | |
|---|---|---|
| DE | 908906 | 4/1954 |
| DE | 3835682 | 4/1990 |
| DE | 3835682 A1 * | 4/1990 |
| DE | 19743048 A1 * | 4/1999 |
| DE | 60114244 | 7/2006 |
| EP | 1582163 | 10/2005 |
| FR | 2787313 | 6/2000 |
| FR | 2848411 A1 * | 6/2004 |
| WO | WO 9707744 A1 * | 3/1997 |

* cited by examiner

*Primary Examiner* — Nicholas Plionis
(74) *Attorney, Agent, or Firm* — Maine Cernota & Rardin (57) ABSTRACT

The present invention relates to an apparatus for the strictly limited flexible stabilization of long bone fractures, said apparatus incorporating a stabilization element configured to be a helical rod that may be introduced into the cavity of a long bone and that comprises a fixation device at one end at least. In accordance with the invention there is provided that the helical rod comprises, beside a very high vertical spring rate, a bending spring rate that is reduced to the "physiological" level as compared to a marrow nail so that, once placed in the bone, minimal healing-promoting movements are being stimulated. It is further preferred that the helical rod has a normalized, uniformly configured head that is independent of the variable outer diameter of the helical rod, which is adapted to the respective bone. Since the head is configured to be uniform and normalized, a uniform tool can be utilized for screwing the rod in, irrespective of the size (diameter) of the helical rod respectively used during surgery. It is also possible to apply the tool in the head region in order to screw the helical spring out again.

11 Claims, 8 Drawing Sheets

APPARATUS FOR STABILIZING LONG BONE FRACTURES

The present invention relates to an apparatus for stabilizing long bone (hollow bone) fractures, said apparatus incorporating a stabilizing element configured to be a helical rod that may be introduced into the cavity of a long bone and that comprises at one end at least a device for manipulation.

In a typical solution known in prior art for stabilizing long bone shaft fractures, one introduces rigid nails. Said nails are either compact or hollow, the marrow space having to be drilled out first, prior to introduction of the nails. In any case, the nails must be driven with great force into the marrow space. The pressure increase generated inside the bone causes particles of marrow debris, fat and blood components to disperse, which may clog the blood vessels, in particular in the lungs and the brain. Moreover, the inner bone texture of the hematopoetic bone marrow, which is also stabilized to a high degree, and the inner blood vessel system are widely destroyed. As a result, bacterial growth is promoted, which explains the increased susceptibility to infection (osteomyelitis) of marrow nailing. In healing, both structures must be built up again in addition to the actual callus, this considerably delaying healing. The rigidity of the nails often results in additional nail-driving fractures on the opposing corticalis, that is to say on the opposite wall of the bone. Fracture gaps driven apart by the nail cannot grow together so that another surgery is needed.

Rigid plates are also used for fixing bone fractures. Like the marrow nails, rigid plates have the disadvantage of preventing natural callus formation. Further, there is the risk that a false joint forms (pseudoarthrosis, "non-union") and that a bone infection develops so that the healing time increases with high probability of a new fracture, once the osteosynthesis material has been removed. As a result, the fracture remains a line of weakness.

An apparatus of the type mentioned herein above is known from DE 38 35 682 C2. In the case of this known apparatus, it is proposed to introduce a kind of helical spring into the shaft of a long bone. This known apparatus has not only been proposed for stabilizing long bone fractures but also for stabilizing joints. This known helical spring was flexible about its longitudinal axis and could be twisted during insertion so that the diameter of the helical spring could be widened or reduced. As a result, the helical spring was still relatively soft and deformable to a certain extent, meaning it still had typical spring properties. In the exemplary embodiments of the printed document such a helical spring is shown, which has been introduced into a femur bone. The spring is shown to be bent along its longitudinal axis.

In the document WO 99/22662 A1, one also utilizes a helical wire thread as the means for osteosynthesis. In this known apparatus, a three-point clamping is proposed, which however is disadvantageous because of the deleterious, fracture displacing forces that are being generated. Moreover, this known apparatus is only intended for subcapital upper arm fractures (fractures occurring directly underneath the epiphysis) and is not intended for shaft fractures. Here also, the helical wire used is still quite soft and elastically deformable. In the stabilization of an upper arm fracture shown in the exemplary embodiments, the helical wire is shown bent at an angle with respect to its longitudinal axis. Moreover, the helical wire is threaded laterally through a bore in the upper arm shaft so that there is an invasive intervention in the bone substance.

The German Patent document DE 908 906 B describes a resilient bone screw, in particular for diagonal and longitudinal fractures, which, as a result thereof is not primarily intended for the marrow space in long bones. This bone screw is referred to as being elastic longitudinally. When screwed in, the spring is biased by being twisted. Next, it is pushed into a drilled hole of the bone and then slackened so that the spring gets wider, that is it widens radially. Accordingly, this helical spring must have enough soft spring properties to allow for these deformations to happen. Once the spring is fixed in the bottom part of the bone, the spring is biased again. Elsewhere in this printed document, it is said that the upper windings of the helical spring can be pushed flat, which is also indicative of elastic deformability.

It is the object of the present invention to provide for a helical rod of the type mentioned herein above that is screwed into the cavity of the long bone and, as a result thereof, into the marrow and only needs minimal invasive surgery, that has, on the one side, advantageous mechanical properties similar to those of a rigid nail and that, on the other side, still allows for minimal movements in the fracture region, which promote bone healing.

The solution to this object is achieved by an apparatus of the type mentioned herein above which has the characterizing features of the main claim.

In accordance with the invention, there is provided that a largely stiff helical rod, which is helical in shape, is being used, said rod having a vertical spring rate set so high that substantially no change in length $\Delta l$ occurs in the longitudinal direction of the helical rod.

The typical vertical spring rate of such a helical rod is for example 1000-6000 N/mm, preferably 1500-5000 N/mm, these values relating to a winding of the helical rod. Furthermore, the bending spring rate of the helical rod is chosen so as to "dynamically" promote osteogenesis.

Callus forms in natural bone healing. Its formation is promoted by small, hardly perceptible movements inside the fracture region. The thus generated alternating pressure and tension forces activate the osteoblasts, the bone building cells. Stiff implants hinder this process. As a result, an almost "dynamic" implant is advantageous for promoting bone healing. A completely stiff marrow nail as it has been used before is biologically disadvantageous. On the other side, it is mechanically advantageous for stabilizing the bone since it lies in the axis of the bone. The helical springs described in prior art have in turn the disadvantage that they are too soft and spring too much so that they do not sufficiently stabilize the fracture mechanically. Years of development within the scope of the present invention have shown that it is possible to best use a helical rod for stabilizing long bone fractures if said rod is sufficiently stiff (and does not spring in the longitudinal direction as a result thereof and if, thanks to its helical shape and in contrast to a conventional marrow nail, it also allows for minimal (physiological) movements in the sub mm range, thus promoting bone healing As contrasted with rigid nails, the asteosynthesis principle for shaft fractures of long bones of the invention, which relies on such a helical apparatus (also referred to as Endo-Helix), has a completely opposite concept in terms of biomechanics: strictly limited flexibility or controlled stiffness (which is however significantly lower than that of a conventional nail) promotes the physiology of bone fracture healing—callus formation through minute movements. The helical rod of the invention is hardly compressible in the direction of its longitudinal axis and is also highly resistant to bending. Although the helical rod has the helical shape of a helical spring, it does not have the typical spring properties and its stiffness is approximately comparable with the helix of a corkscrew.

The helical rod of the invention is a helical rod bent in a spiral shape (helix shape) by cold deformation for example of a wire or of a rod the discrete windings of which are spaced apart. Because of the great stiffness of the helix in the axial direction (vertical spring rate) it is not possible to compress the helical rod by exerting a pressure in the axial direction. As contrasted to a helical spring, the windings of the helical rod remain spaced apart. The helix of the helical rod of the invention preferably has a relatively large pitch. This pitch may for example be chosen such that the vertical value for a complete 360° winding of the helix is greater than the outer diameter of the helix. For application in surgery, there exist helical rods having different outer diameters since different sizes are needed because of the different dimensions of the bones. Also, the thickness of the wire from which the helix is bent may vary so that the inner diameter also varies.

There still remains a minimal residual flexibility across the axis of the helical rod, which suffices to achieve the desired physiological effect. The bending spring rate is chosen such that bendings transverse to the axis of the helical rod are possible in the range of less than 1 mm or of fractions of millimeters, these bendings are sufficient for the physiological effect. The helical rod has the property of stretching (not that of lengthening axially) but of orienting itself in the longitudinal direction of the bone axis. This allows for keeping the bone axis stable while still allowing for minimal movements in the fracture region in order to activate callus formation. Through the only minimal but physiologically still effective flexibility it is possible to use the minimal movements for accelerating bone healing. Clinical follow-ups have shown that outstanding callus formation is possible in relatively short time.

Through the sufficient stiffness of the helical rod, it is not only possible to screw it into the marrow space by means of an appropriate tool applied in the upper region (without having to remove the bone marrow), but also to remove it again after healing by turning it in the opposite direction. In contrast to the known solutions, the helical rod cannot be twisted and is neither clamped not widened radially in order to fix it in the marrow space. It suffices to simply screw it into the bone marrow since the helical rod remains in its position in the bone marrow almost through self-support by virtue of its inherent stiffness. Minimal invasive surgery may be used to introduce it since cuts of merely about 3 cm in length are needed. The fractures stabilized in this way heal much faster than with other methods and this method involves less complication since surgery causes less damage and since the haematopoietic and osteoblastic tissue is preserved.

Hitherto, with the known apparatus, the upper part of the helical spring, which protruded from the bone, was cut. This involved difficulties both when definitively screwing the helix in and when unscrewing it again, once the bone had healed. The helix of the invention, by contrast, allows for placement by simplified, standardized surgery and can be readily unscrewed and removed after bone healing is complete.

In accordance with a preferred developed implementation of the invention there is provided that the helical rod comprises a normalized uniformly configured head that is independent of the variable outer diameter of the helical rod, which is adapted to the respective bone and that at least one pin is located on the head, which projects approximately axially and which is formed from the first winding of which it is an integral part. The diameter of the helical rod must be adapted to the size of the marrow space which may vary within wide ranges since children's bone fractures are also stabilized. As a result, the manufacturer must provide the surgeon with a choice of helical rods of different sizes. For each of these sizes, a respective adapted tool would be necessary to manipulate the helical rod. This is avoided by the head of the helical rod according to the developed implementation of the invention, which is standardized in size and in shape.

Unlike hitherto, one now proceeds as follows for placing the apparatus of the invention: After having determined the length needed such as by x-rays prior to screwing the helical rod, the lower end of the helical rod is cut with an appropriate tool (such as a bolt cutter), thus cutting it to the required length. As a result, the head of the helical rod remains preserved at its other end, which forms the screwing region. Then, only one additional tool suffices to screw said rod into the long bone, this tool being applied to the axially protruding pin. Since the head is configured uniformly and standardized, a unitary tool can be utilized, irrespective of the size (diameter) of the helical rod respectively used in surgery. It is this very pin in the head region one takes hold of in order to again unscrew the helical rod.

According to a possible variant of the solution to this object, there is preferably provided that the helical rod comprises a tapering or flaring diameter over one portion of its length at least. Under its head the helical rod can have an upper portion with an outer diameter that tapers away from the head end. Such a for example approximately funnel-shaped portion can be used advantageously in case of osteoporosis or of strongly widened marrow spaces. On such a helical rod, said conical portion (funnel portion) can be adjoined with a cylindrical portion of constant outer diameter.

It is just as well possible that the outer diameter and the pitch of the helical rod are constant over its length. Such an embodiment may for example also be used if greater loads have to be absorbed. In this case, two of these identically designed helix-shaped helical rods can be screwed into each other so that their windings extend parallel to each other.

As compared to the prior art solutions, a helical rod is used in accordance with the invention, which is of considerably stiffened construction and which preferably has a vertical spring rate set to range between 1500 and 5000 N/mm, that is so high that no spring effect occurs in the longitudinal direction (no change in length $\Delta l$). Furthermore, the bending spring rate was also preferably lowered to a range that only allows for "physiological" bending deflections. This bending spring rate defines the bending of the helical rod across its longitudinal extension. It is to be noted here that the helical rod introduced in the marrow space behaves differently from a bare helical rod. The helical rod of the invention however differs from the known marrow nail with an extremely high bending spring rate, said known marrow nail not allowing for any bending and thus suppressing any natural healing stimulus that might be given to the fracture. Depending on the outer diameter, the bending spring rate of the helical rod of the invention of a length of 300 mm for example, when clamped on the one side and bent through at the other end, ranges between 250 and 1250 mN/mm, preferably between 300 and 1250 mN/mm (millinewton per mm). As compared herewith, a conventional marrow nail has bending spring rates ranging between 5000 and 15000 mN/mm. The bone takes note of the marrow nail as a "stiff component part" that does not generate any healing promoting stimulus.

According to a preferred developed implementation of the invention, one uses a helical rod that comprises, at least in portions, a roughened surface. This facilitates the ingrowth of the apparatus in those cases in which it is not intended to be removed so as to serve as a permanent stabilizer such as in elder patients.

Another preferred developed implementation provides that the helical rod is bevelled in the region of its tip, both on the inner side of the helix and on the outer side of the helix. As a result, one obtains a physiologically advantageous, self-cutting front end, said front end and possible bone splitters being pushed aside in the inward direction so as not to hinder further screwing.

Another object of the present invention is a device for fixing to a long bone an apparatus of the invention of the type described herein above, said device incorporating a strap-like or otherwise configured fixture that comprises on the outside, on the bone surface, at least one fastening region for fixation with fastening elements as well as a reception region for receiving the one end of the helical rod, which traverses the wall of the bone. One thus obtains an adapted device for fixing to the bone surface the helical rod, which has been shortened at need, said device being in particular suited for special forms of fractures located underneath the epiphysis of the upper arm (subcapital upper arm fractures). The strap-like device may for example be fixed to the bone by means of screws without said device being loaded.

The helical rod used in accordance with the invention can for example be made from wires of any cross section, preferably having a round or an ellipsoidal cross section. In accordance with the invention it is stiffened so as no longer to be suited for stabilizing joints. The windings of the helical rod are not allowed to lie on top of each other since the helical rod would then become too soft. If the helical rod bends too much, the fracture moves too much, thus hindering healing. Then, there is a risk of pseudoarthrosis and an additional plaster cast would be necessary. It is particularly preferred that the helical rod of the invention is made from special spring steel having a higher modulus of elasticity than titanium for example. The use of titanium would require a larger outer diameter and a thicker wire, which is out of the question since the marrow spaces are too narrow therefor. In accordance with the invention a 1.4441 steel alloy is particularly well suited for example.

In providing a helical rod for stabilizing long bone fractures in accordance with the invention, different parameters influence the properties such as the vertical spring rate and the bending spring rate, said parameters being in particular the pitch of the helix, the thickness of the wire, the outer diameter of the helical rod and the material from which the helical rod is made. At need, the method of manufacturing the helical shape by deforming a wire or a rod also plays a part. The outer diameter varies as a function of the size of the bone to be stabilized. The wire thickness and the pitch can be varied to set the vertical spring rate. Possible exemplary dimensions for a helical rod that is suitable for an apparatus of the invention are for example, for a length of 250-300 mm, an outer diameter of 8-15 mm, a wire thickness of 2-4 mm, an inner diameter of 4-9 mm and a pitch of 15-20 mm for each winding.

The features mentioned in the dependent claims relate to preferred developed implementations of the solution to the object of the invention. Other advantages of the invention will become apparent from the following detailed description.

The invention will be understood better upon reading the exemplary detailed description accompanying the appended drawing wherein.

At first, reference will be made to FIG. 1. The illustration shows to an enlarged scale the upper part of a helical rod 10 of the invention, which is pushed into the long bone in case of a bone fracture. This helical rod 10 has an outer diameter d that may vary, depending on the size of the respective long bone into which the helical rod is being introduced. The pitch of the helical rod 10 may also vary, depending on the case of application. The lower part of the helical rod 10 is not shown in the drawing since it is devised in analogous fashion and since the windings continue in the same way. The respectively needed length is determined prior to use and the helical rod is accordingly cut to length at its lower end. The cross section of the wire from which the helical rod 10 is made in the exemplary embodiment is round but may also be of almost any design in principle. The helical rod 10 consists of a metal wire of a special steel alloy (such as 1.4441), which is suited for medical application and which exhibits high rigidity. Accordingly, it is not a spring that is elastic when stretched lengthwise and then returns to its initial position like a tension spring. Instead, the rigidity is so high that almost no longitudinal stretching (or compression in longitudinal direction) occurs.

Figure 1:
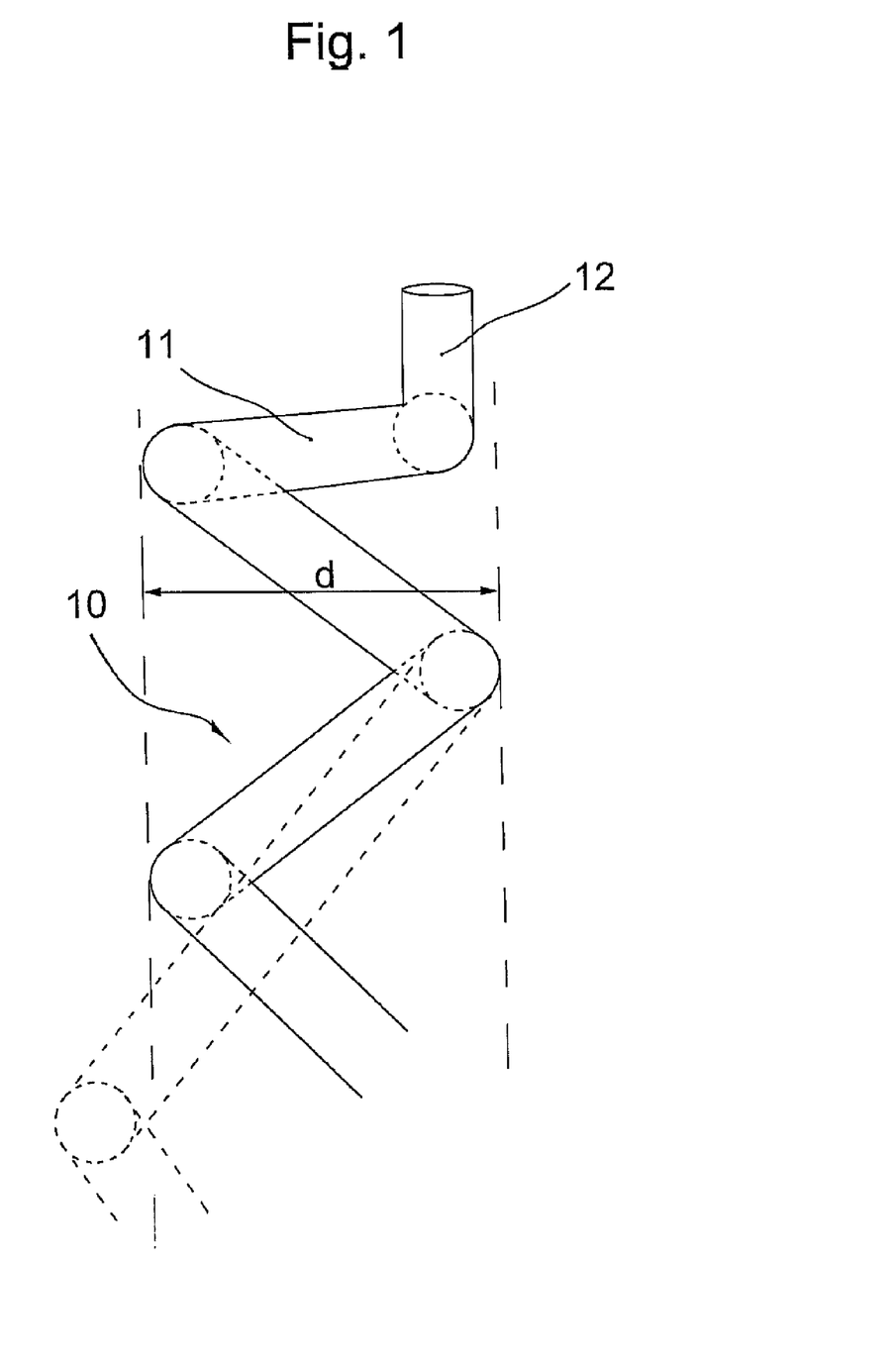
FIG. 1 is a schematically simplified illustration of a part of an apparatus of the invention in an exemplary implementation variant.

As can be seen from FIG. 1, the upper winding 11 is a compressed winding in the upper end region (head region) of the helical rod, that is, a winding with a lesser pitch than the other windings. A pin 12 oriented in the axial direction then adjoins the uppermost compressed winding 11, said pin serving as a point of application when screwing the helical rod in with a specific tool as will be explained in closer detail herein after. In this head region with the uppermost winding 11 and the axially oriented pin 12, which protrudes from the spring end, the helical rod 10 is normalized. This means, this head region has always the same design and dimensions, irrespective of the respective outer diameter and of the pitch of the helical spring. The two last mentioned variables may vary in accordance with the case of application. Since however the head region is always of the same design, a unitary tool may always be used during surgery for manipulating the helical rod 10.

Figure 2:
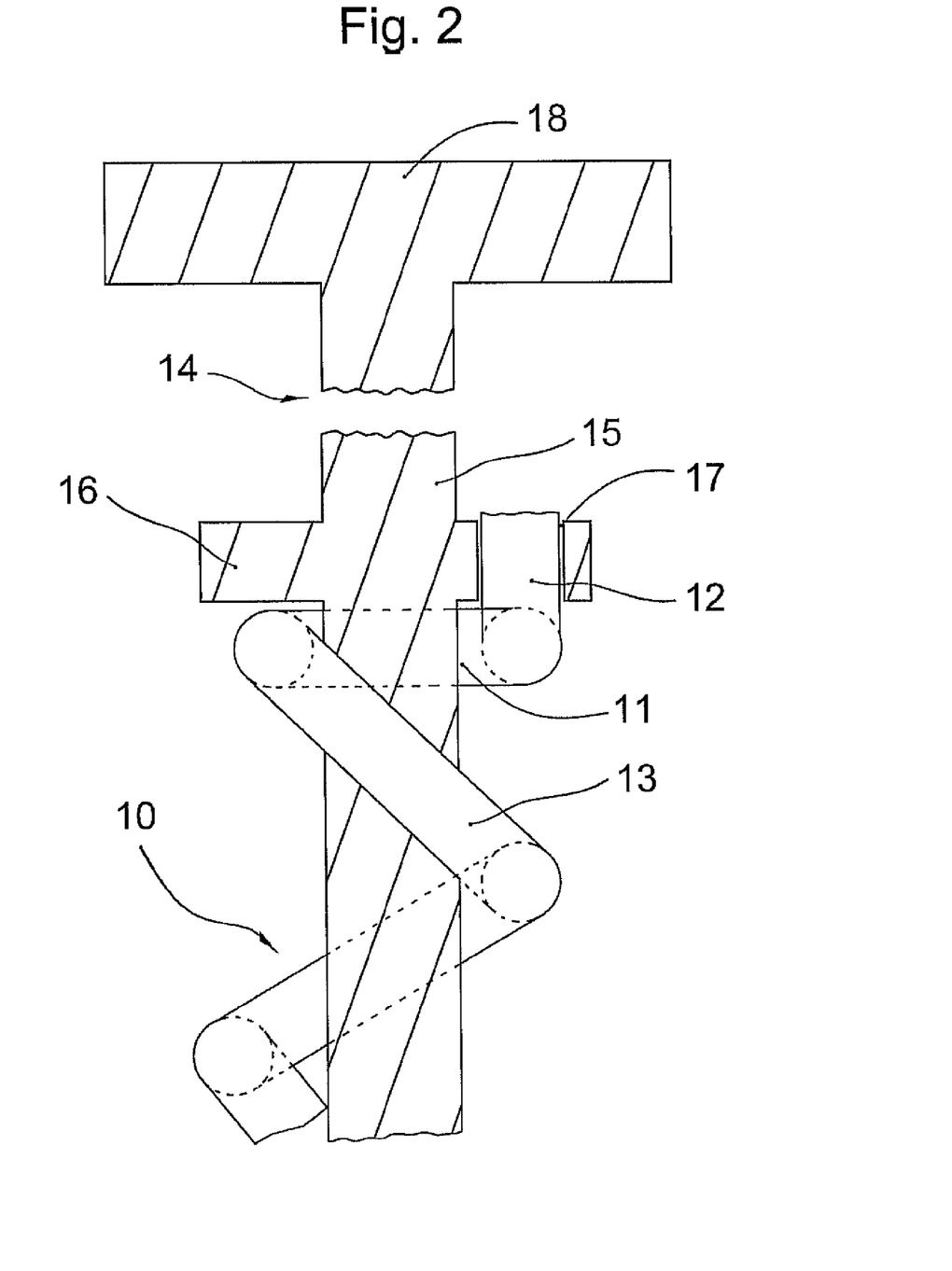
FIG. 2 is a schematically simplified illustration, to an enlarged scale, showing more clearly the way the helical rod is twisted by means of a tool.

Referring now to FIG. 2, the process of screwing the helical rod into the long bone during surgery will be explained in closer detail herein after. The illustration shows the head region of the helical rod 10 to a scale slightly enlarged from FIG. 1. The second uppermost winding 13 and the end side compressed winding 11 with the axially protruding pin 12 can be seen. The tool 14 used has a shaft 15 with an element 16, which is for example configured like a plate of radial extension and which may for example be configured to be annular like a collar or also rectangular in the form of a plate or of a transverse pin. In this radial element 16, there is located a hole 17 or a recess into which the axially protruding pin 12 of the helical rod can be introduced. At the same time, the lower portion of the shaft 15 serves as a centering means for the tool 14 since it engages coaxially into the helical rod 10 in the head region thereof, as can be seen herein. At the end of the shaft 15 of the tool 14 there is located a grip 18 that can be taken hold of in order to turn the tool 14 about its axis. The pin 12 is entrained thereby and the helical rod 10 is caused to rotate together with it. For removal, the same tool 14 can be used and can be screwed out of the bone by rotating the helical rod in the reverse direction.

Instead of rotating the tool 14 by hand, it may be advantageous to operate it through a mechanical apparatus suited for rotating the tool at a relatively small rpm. In this case, coupling means that have not been illustrated herein are provided in the upper portion in the head region 18 of the tool 14, said coupling means cooperating with corresponding coupling means on the mechanical screwing apparatus; this may for example be a hexagon socket, an allen or another surface of application on the tool. The advantage of this variant over manual operation is that it is not necessary to regrasp the tool after each half rotation, which would interrupt the screwing process and which could possible be disadvantageous.

Figure 3:
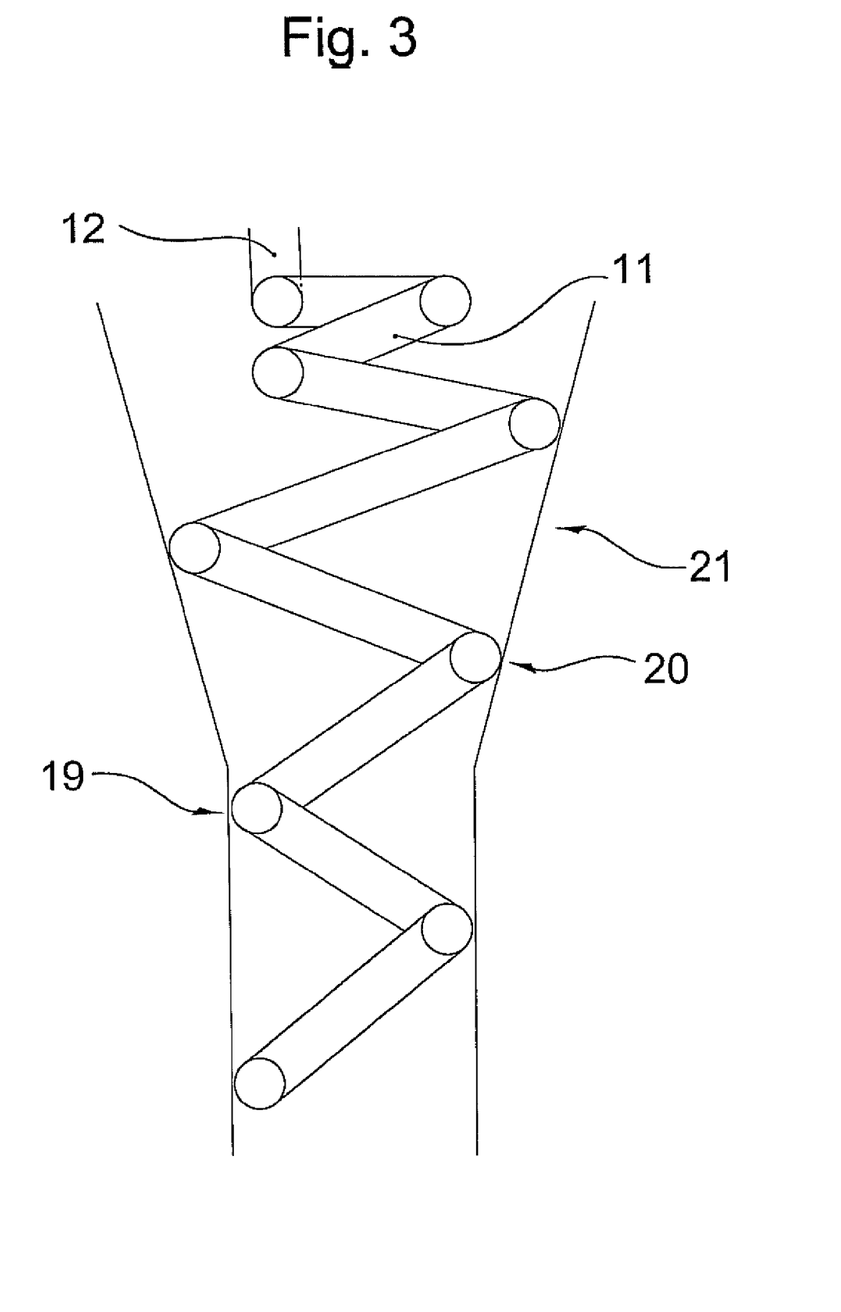
FIG. 3 is a schematically simplified illustration of the upper part of a helical rod in accordance with an alternative implementation variant of the invention.

Referring now to FIG. 3, an alternative exemplary embodiment of the present invention will be explained in closer detail herein after. It shows a variant of the helical rod 20 wherein, unlike in the exemplary embodiment described herein above, the outer diameter of the helical rod is not constant in the upper region. Here, a cylindrical portion 19 is provided which is adjoined axially in the upper region with a funnel portion the outer diameter of which flares conically upward toward the head end of the helical rod. Accordingly, the diameter of the helical rod increases progressively toward the head end in this funnel region 21, which is advantageous in certain applications like for example in the case of widened marrow spaces. The funnel portion 21 is then also adjoined with the normalized head region with the compressed winding 11 and with the axially oriented pin 12 so that the helical rod 20 can be operated in analogous fashion to the already described helical rod 10 according to the exemplary embodiment shown in the FIGS. 1 and 2.

Figure 4:
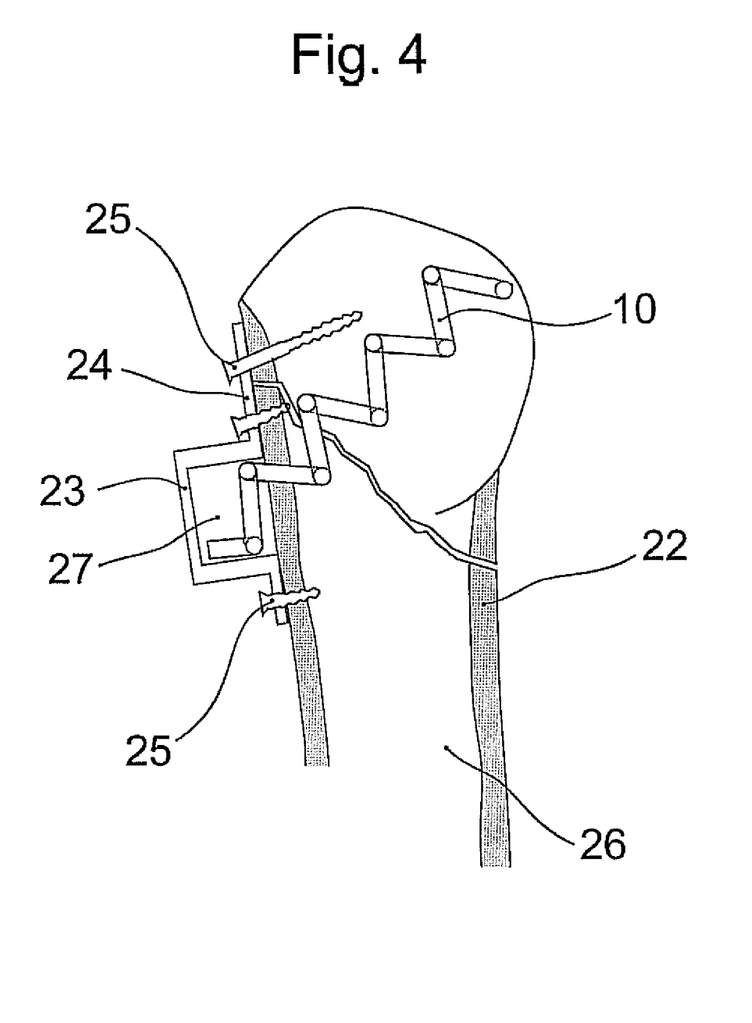
FIG. 4 is a schematically simplified illustration for explaining the application of a possible alternative implementation variant of the apparatus of the invention.

Referring to the FIGS. 4, 4a and 4b, another exemplary embodiment of the present invention will be explained in closer detail herein after. FIG. 4 shows in a schematically simplified view a section through a part of a long bone 22. There is shown a strap-like fixture 23 by means of which one end of a helical rod 10 of the invention can be fixed in the wall of a long bone 22. For this purpose, this fixture 23 has portions 24 that come into abutment against the outer side of the long bone where they can be fixed by fastening elements 25 such as screws. The end of the helical rod 10 which is to be fixed, extends through a bore in the bone whilst the rest of the helical rod 10 extends in the cavity 26 of the long bone. The strap-like fixture 23 has a central portion 27 in the shape of a sheath or of a socket that forms for example a cylindrical receptacle between the fixture and the outer side of the long bone, said receptacle receiving the end of the helical rod 10 which extends beyond the wall (meaning outside of the long bone 22) so that this end can be fixed by the fixture 23.

Figure 4A:
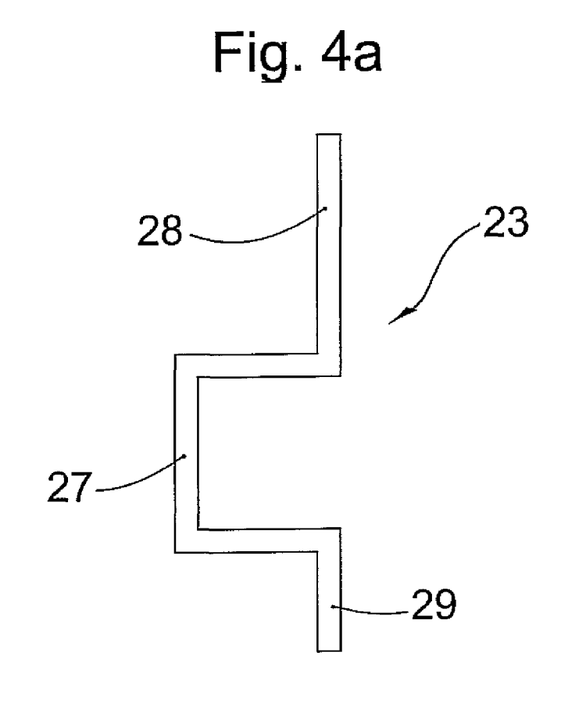
FIGS. 4a and 4b each are detailed views of the strap-shaped fixture used in the variant shown in FIG. 4 for fixation to the bone.
Figure 4B:
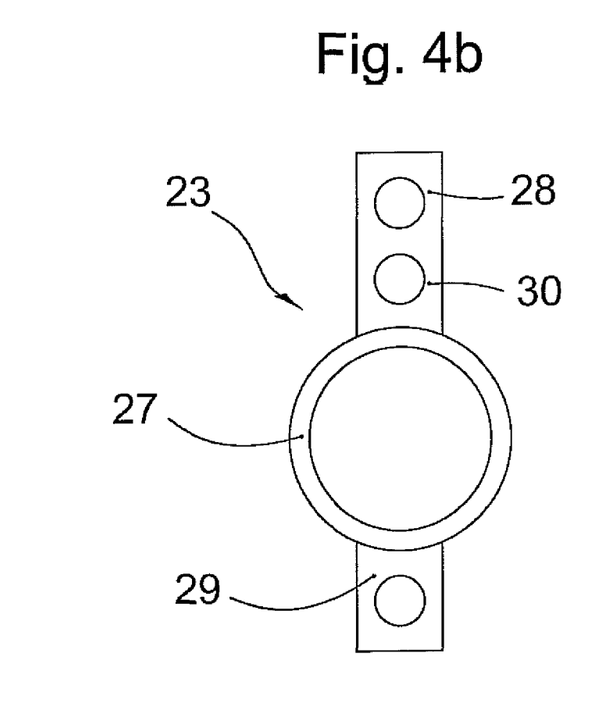

The FIGS. 4a and 4b show once more the strap-like fixture 23 alone in a side view and in a top view. The shape with the crank (in the side view FIG. 4a) through which the central sheath-like portion 27 with its approximately cylindrical receptacle is formed can be seen therein. This central portion 27 is adjoined on either side with a respective strap 28, 29 with threaded holes 30. As can be seen in FIG. 4, these straps abut the outer side of the wall of the bone when fastened so that they can be fastened to the bone through screws 25 and so that the strap-like fixture 23 can be generally fixed to the bone.

Figure 5:
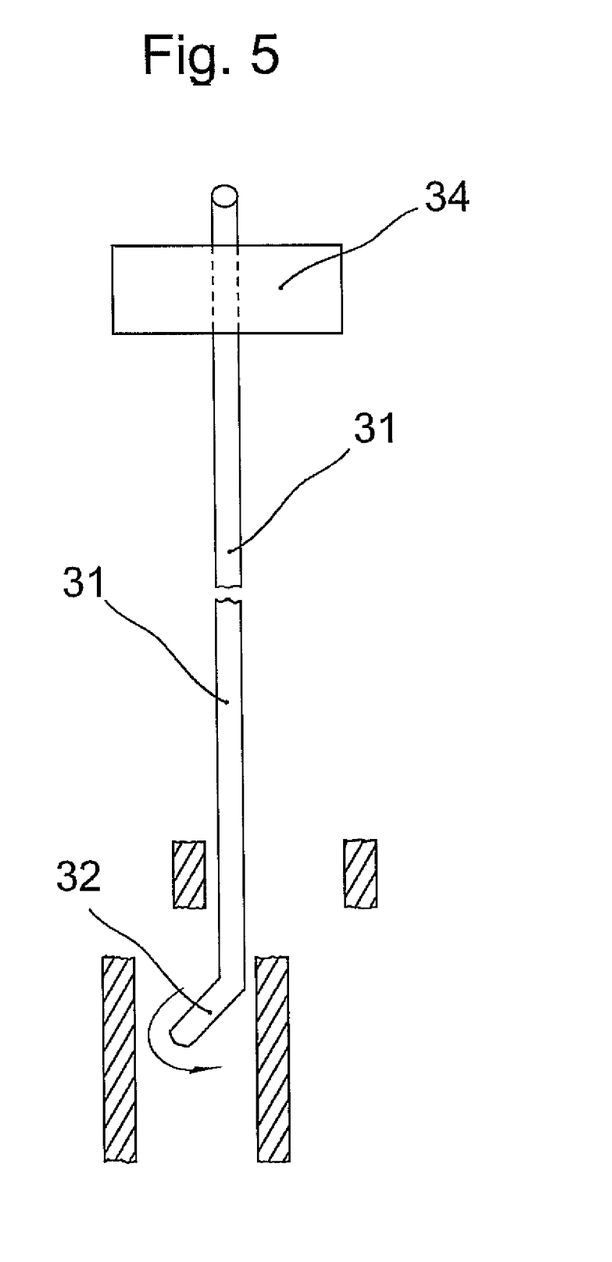
FIG. 5 shows an appliance used for aligning the displaced fracture ends (repositioning rod)
Figure 6:
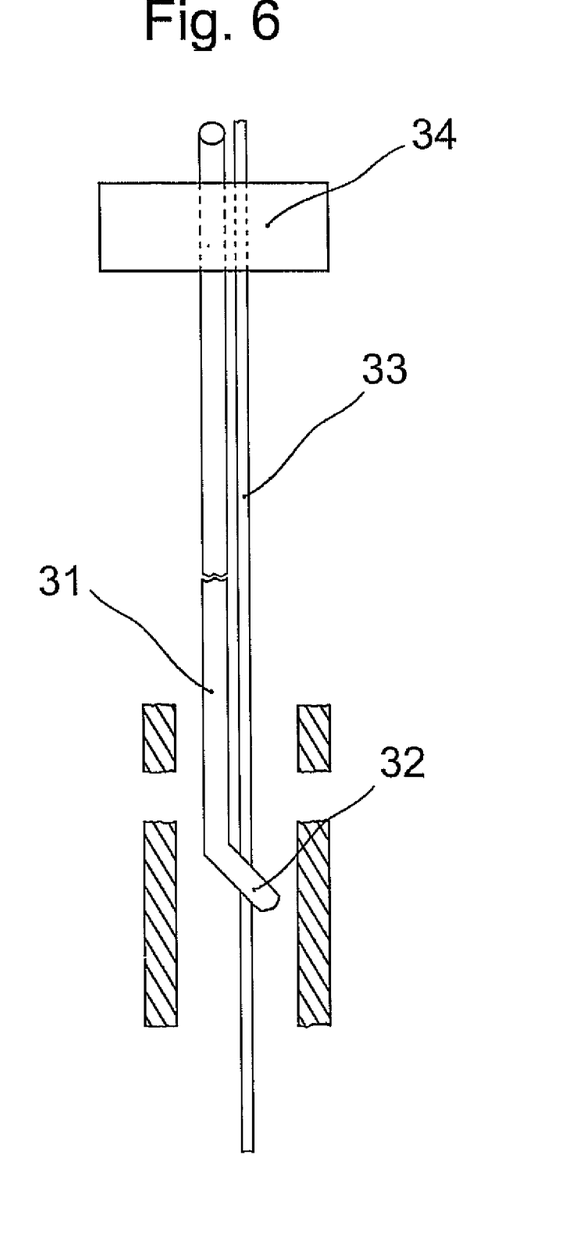
FIG. 6 shows another appliance (guide rod) that is introduced prior to screwing the helical spring.

Referring to the FIGS. 5 and 6, specific tools will be explained herein after, which one should use for positioning a helical rod of the invention. FIG. 5 shows what is referred to as a repositioning rod 31 used for aligning displaced fracture ends. It is an elongate rod made from steel for example, which has an angled portion 32 at its tip. Prior to introducing the helical rod 10, it is guided for rotation as far as into the lower fractured bone portion. Upon completion of alignment through rotation of the repositioning rod 31, a second, thinner rod, which is referred to as a guide rod 33 and which is shown in FIG. 6 and which is also usually made from stainless steel, is introduced as far as into the lower fragment beside the repositioning rod 31. This guide rod almost serves as a guide for the helical rod 10 which should only be screwed in through this guide rod 33. This serves to ensure that no nerve or vessel will be injured during introduction of the helical rod. Both rods 31, 33 can be guided with a grip 34. The sketch shown in FIG. 5 illustrates how the lower end with the angled portion 32 aligns the displaced fracture ends. FIG. 6 illustrates the relative position of the two rods 31 and 33 after introduction thereof into the long bones before screwing the helical rod in.

Figure 7:
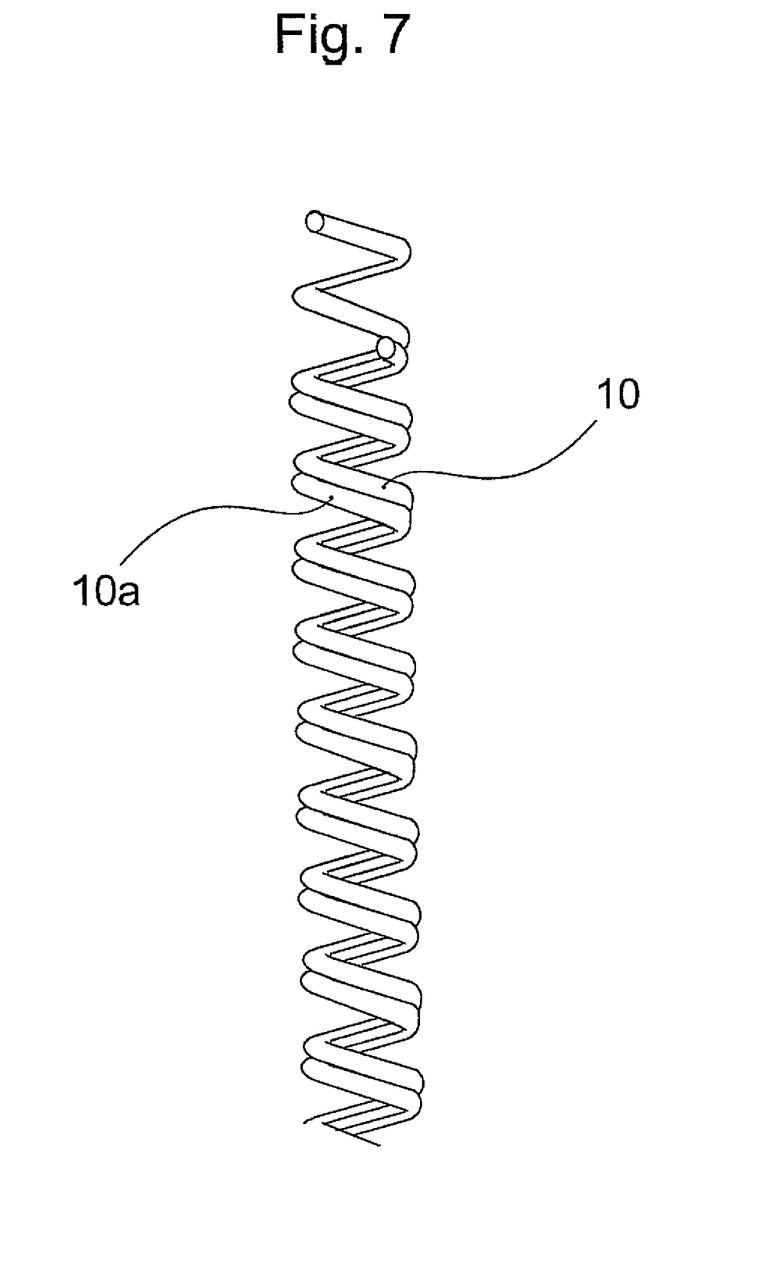
FIG. 7 shows a double helical rod which is utilized in certain cases of application in accordance with an alternative variant of the invention.

Referring to FIG. 7, another alternative exemplary embodiment of the present invention will be explained herein after in closer detail. In this variant, a double helical rod is used in order to neutralize greater loads for example. If one uses a first helical rod 10 of a design as described herein above with reference to FIG. 1, and if one then screws thereinto an identically designed second helical rod 10a having the same outer diameter and the same pitch, one obtains a double rod as shown in FIG. 7. Both helical rods lie almost inside each other so that their windings extend parallel to each other. The thus obtained double rod has a stiffness which is twice that of a single helix, this making it possible, as mentioned above, to take greater loads and further reducing the compliance of the helical rod during movements of the bone.

There are different alternative tools that may also be used for screwing a helical rod of the invention into a long bone. The end of the uppermost winding of the helical rod can be bent radially inward for example. An accordingly shaped tool, the shape of which conforms to the shape of the thus obtained hollow space (C shape) inside the helix, may then interlockingly engage into this cavity in the winding so that rotational engagement occurs.

Alternatively, the head region of the helical rod may also be ground on the outer side so as to obtain a square or a polygonal shape for example. With a key-like tool of an appropriate shape having a square or a polygonal socket, one can take hold of the rod by the head of the helix, thus establishing the rotational engagement.

It is also possible to weld a body onto an uppermost, flattened winding of the helical rod, said body having for example the shape of a polygon that can be taken hold of with an allen key for rotating the helix.

Alternatively, it is also possible for example to obviate the need for a head of a specific shape on the helix and to straddle with a tool an upper portion of the helix from the outside, said tool having a kind of chuck that is radially adjustable, thus clampingly taking hold of the upper portion of the helix.

List of Numerals 10 helical rod
10a second helical rod
11 compressed winding
12 pin
13 second uppermost winding
14 tool
15 shaft
16 radial element
17 hole
18 grip
19 cylindrical part
20 helical rod
21 funnel portion
22 long bone
23 strap-like fixture
24 portions for fastening
25 fastening elements
26 cavity
27 central portion
28 strap
29 strap
30 threaded holes
31 repositioning rod
32 angled portion
33 guide rod
34 grip
35 grip

The invention claimed is:

1. An implantable apparatus for internally stabilizing long bone fractures, said apparatus comprising:
  a helical rod configured for placement into a marrow cavity of a long bone in a lengthwise direction by a manipulation device, the helical rod having a vertical spring rate in a range of about 1500-5000 N/mm to provide the helical rod with a high rigidity such that no change in length occurs in a longitudinal direction of the helical rod when the helical rod is in the marrow cavity of the long bone;
  the helical rod having a bending spring rate that allows bending of the helical rod transverse to its longitudinal direction in a range of less than 1 mm, the helical rod being a section of helical rod material having a bending spring rate chosen such that a 300 mm length of said helical rod material, if clamped at a proximal end thereof, would exhibit a force-to-deflection ratio at a distal end thereof ranging between about 250 and 1250 mN/mm;
  the helical rod further comprising a head forming a screwing region, the head being adapted to the long bone and having a diameter which is independent of an outer diameter of the helical rod.

2. The apparatus as set forth in claim 1, wherein said helical rod comprises, in a region of the head, a lesser pitch over a circumference of at least one winding of the helical rod.

3. The apparatus as set forth in claim 1, wherein at least one pin protrudes approximately longitudinally from the head, said at least one pin being formed from a first winding of the helical rod, and being connected to and integral with the head.

4. The apparatus as set forth in claim 1, wherein the helical rod comprises a roughened surface, at least in parts of the helical rod.

5. The apparatus as set forth in claim 1, wherein the helical rod comprises a self-cutting tip in a front end region of the helical rod, said self-cutting tip being formed by a bevel on an inner side and on an outer side of the helical rod.

6. The apparatus as set forth in claim 1, wherein a wire thickness of the helical rod is in a range of about 2-4 mm.

7. The apparatus as set forth in claim 1, wherein a pitch for each winding of the helical rod is in a range of about 15-20 mm.

8. The apparatus as set forth in claim 1, wherein the length in the longitudinal direction of the helical rod is in a range of about 250-300 mm.

9. The apparatus as set forth in claim 1, wherein an outer diameter of the helical rod is in a range of about 8-15 mm.

10. The apparatus as set forth in claim 1, wherein an inner diameter of the helical rod is in a range of about 4-9 mm.

11. The apparatus as set forth in claim 1, wherein the helical rod comprises wire of a 1.4441 steel alloy.

* * * * *